United States Patent
Roberts

(10) Patent No.: US 7,512,431 B2
(45) Date of Patent: *Mar. 31, 2009

(54) NORMALIZATION METHOD FOR A CHRONICALLY IMPLANTED OPTICAL SENSOR

(75) Inventor: Jonathan P. Roberts, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 484 days.

This patent is subject to a terminal disclaimer.

(21) Appl. No.: 11/225,591

(22) Filed: Sep. 13, 2005

(65) Prior Publication Data

US 2007/0060811 A1    Mar. 15, 2007

(51) Int. Cl.
*A61B 5/1455* (2006.01)

(52) U.S. Cl. .................. 600/332; 600/325; 600/333; 600/339

(58) Field of Classification Search .............. 600/323, 600/325, 327, 332, 339, 341
See application file for complete search history.

(56) References Cited

U.S. PATENT DOCUMENTS

| | | | |
|---|---|---|---|
| 3,847,483 A | 11/1974 | Shaw et al. | |
| 4,114,604 A | 9/1978 | Shaw et al. | |
| 4,202,339 A | 5/1980 | Wirtzfeld et al. | |
| 4,467,807 A | 8/1984 | Bornzin | |
| 4,523,279 A | 6/1985 | Sperinde et al. | |
| 4,623,248 A | 11/1986 | Sperinde | |
| 4,815,469 A | 3/1989 | Cohen et al. | |
| 5,730,125 A * | 3/1998 | Prutchi et al. | 600/323 |
| 6,125,290 A | 9/2000 | Miesel | |
| 6,198,952 B1 | 3/2001 | Miesel | |

FOREIGN PATENT DOCUMENTS

WO    WO0025860    5/2000

* cited by examiner

*Primary Examiner*—Eric F Winakur
*Assistant Examiner*—Etsub D Berhanu
(74) *Attorney, Agent, or Firm*—Michael C. Soldner

(57) ABSTRACT

A system and method are provided for estimating blood oxygen saturation independent of optical sensor encapsulation due to placement in blood, where the blood includes a blood flow characteristic of: a relatively low, a stasis, a stagnant value. The method includes determining tissue overgrowth correction factor that includes optical properties of the tissue that cause scattering of the emitted light to a detector and relative amplitudes of the emitted light wavelengths. A corrected time interval measured for infrared light is based on an infrared signal and a corrected time interval for red light is determined by subtracting red light signal due to presence of tissue overgrowth. The red light signal due to tissue overgrowth is proportional to total infrared signal less nominal infrared signal. Oxygen saturation is estimated based on standard calibration factors and the ratio of the corrected infrared time interval and the corrected red time interval.

18 Claims, 5 Drawing Sheets

NORMALIZATION METHOD FOR A CHRONICALLY IMPLANTED OPTICAL SENSOR

CROSS REFERENCE TO RELATED APPLICATIONS

This present patent disclosure is a continuation of that certain co-pending application of common title which issued to Jonathan Roberts on 13 Sep. 2005 as U.S. Pat. No. 6,944,488, the contents of which are incorporated herein by reference.

FIELD OF THE INVENTION

The present invention relates generally to the field of implantable optical sensors and more specifically to a method for providing accurate optical sensing of blood oxygen saturation in the presence of tissue overgrowth on the optical sensor; in particular the invention provides significant utility when directed toward volume of blood and said blood has a characteristic flow-rate which in exemplary embodiments includes one of a relatively low rate, a stasis rate, a stagnant rate.

BACKGROUND OF THE INVENTION

Implantable medical devices (IMDs) for monitoring a physiological condition or delivering a therapy typically rely on one or more sensors positioned in a patient's blood vessel, heart chamber, or other portion of the body. Examples of IMDS include heart monitors, pacemakers, implantable cardioverter-defibrillators (ICDs), myostimulators, nerve stimulators, drug delivery devices, and other IMDs where such sensors are desirable. Implantable sensors used in conjunction with an IMD generally provide a signal related to a physiological condition from which a patient condition or the need for a therapy can be assessed.

Measurement of blood oxygen saturation levels are of interest in determining the metabolic state of the patient. Generally, a decrease in blood oxygen saturation is associated with an increase in physical activity or may reflect insufficient cardiac output or respiratory activity. Thus monitoring blood oxygen saturation allows an implantable medical device to respond to a decrease in oxygen saturation, for example by pacing the heart at a higher rate. An implantable oxygen sensor for use with an implantable medical device is generally disclosed in commonly assigned U.S. Pat. No. 6,198,952 issued to Miesel, hereby incorporated herein by reference in its entirety. Cardiac pacemakers that respond to changes in blood oxygen saturation as measured by an optical sensor are generally disclosed in U.S. Pat. No. 4,202,339 issued to Wirtzfeld and in U.S. Pat. No. 4,467,807 issued to Bornzin.

One limitation encountered with the use of implantable optical sensors can arise as the result of tissue encapsulation of the sensor that occurs as a result of the body's normal response to a foreign object. If an optical blood oxygen sensor is positioned in an area of relatively high blood flow, tissue encapsulation of the sensor may not occur or may at least be minimized to a thin collagenous sheath. If a blood oxygen sensor resides in an area of relatively low blood flow or a stagnant area, tissue encapsulation is likely to occur and the capsule may become relatively thick. Such tissue overgrowth interferes with the performance of the sensor in accurately measuring blood oxygen or other metabolites by reducing the (light) signal to noise ratio. For example, the light signal associated with blood oxygen saturation is reduced due to attenuation of emitted light from the optical that reaches the blood volume and attenuation of the reflected light from the blood volume reaching a light detector included in the optical sensor. Noise due to extraneous light reaching the light detector is increased by the scattering of emitted light by the tissue overgrowth.

The time course and degree of tissue encapsulation of an optical sensor, or any other medical device implanted within the blood volume, is uncertain. Thrombus formation in the vicinity of the sensor due to blood stasis or endothelial injury can occur at unpredictable times after device implant. If the thrombus is in contact with the endocardium or endothelium, macrophages can invade the clot, phagocytose the blood cells and orchestrate collagenous encapsulation by fibroblasts. Because the time course and occurrence of these events is unpredictable, the reliability of blood oxygen saturation measurements at any point in time may be uncertain.

One approach to solving the problem of tissue overgrowth is generally disclosed in U.S. Pat. No. 6,125,290 issued to Miesel, incorporated herein by reference in its entirety. A self-test light detector is provided for estimating the amount of light reflected back into a light emitter portion instead of being transmitted through a lens for reflection from a blood volume. An output signal from self-test light detector may be employed to calibrate or adjust the output signal provided by a light detector in a manner that the estimate of blood oxygen saturation is compensated or adjusted to account for the degree or amount of tissue overgrowth of the sensor.

A need remains, however, for a method for adjusting a blood oxygen saturation (or other metabolite) measurement to account for extra light intensity associated with light scattering tissue or thrombus over the oxygen sensor, and the like. The method preferably provides accurate blood oxygen saturation measurement independent of the presence of tissue overgrowth.

SUMMARY OF THE INVENTION

In an exemplary embodiment, an implantable optical sensor system and method are provided for accurately estimating blood oxygen saturation independent of the presence of tissue encapsulation of the optical sensor. According to the present invention, dual wavelength radiation is used to beneficially provide a first wavelength signal substantially independent of the presence of a metabolite and a second wavelength signal is substantially dependent upon the presence of said metabolite.

Thus, in the exemplary embodiment, a two wavelength optical sensor is employed wherein the amount of reflected light from one wavelength, typically red, is dependent on oxygen saturation, and the second wavelength, typically infrared light, is independent of oxygen saturation. A time interval is measured for each light wavelength as the current induced on a sensor (e.g., a photodetector) in response to the intensity of the reflected light integrated over a capacitor included in the photodetector. The time interval measured for the red light signal is normalized by the time interval measured for the infrared light signal to account for differences in hematocrit and blood flow velocity.

The method includes calculating a corrected time interval measured for the red light signal and a corrected time interval measured for the infrared light signal to account for the presence of tissue overgrowth. A tissue overgrowth correction factor is used in calculating a corrected red light time interval which accounts for: 1) the optical properties of the tissue that cause scattering of the emitted light to a light detector determined experimentally, and 2) the relative amplitudes of the emitted light wavelengths from the optical sensor (e.g., as determined at the time of device manufacture). A corrected time interval measured for infrared light is determined based on the nominal infrared signal returned from an inspected volume of blood in the absence of tissue overgrowth (e.g., as determined at the time of device manufacture). A corrected time interval measured for red light is determined by subtracting the amount of red light signal attributed to the presence of tissue overgrowth from the total red light signal. The amount of red light signal attributed to the presence of tissue overgrowth is calculated by multiplying the total infrared signal (less the nominal infrared signal) by the tissue correction factor. Oxygen saturation is estimated based on standard calibration factors and the ratio of the corrected infrared time interval and the corrected red time interval.

DETAILED DESCRIPTION OF THE INVENTION

The present invention is directed at providing a method for accurately measuring changes in blood oxygen saturation using a chronically implantable optical sensor. In particular, the present invention provides a method for compensating for extra light intensity detected by the optical sensor due to light scattering matter, typically collagenous tissue or thrombus, which may be present over the sensor. The methods included in the present invention employ a two-wavelength system and a correction method that allows the extra light intensity due to light scattering tissue over the sensor to be compensated for in calculating oxygen saturation.

Two-wavelength optical sensing systems are known for use in the field of blood oximetry. See for example, U.S. Pat. No. 3,847,483 issued to Shaw et al. In a two-wavelength system, the reflected light signal of one wavelength that changes in intensity with blood oxygen saturation is normalized by a second wavelength of which the reflected intensity is independent of blood oxygen saturation but dependent on other physiological changes in the measured blood volume, such as blood flow velocity and hematocrit concentration. The methods included in the present invention provide an additional correction method to account for additional light signal detected due to tissue overgrowth. The intensity of both wavelengths in a two-wavelength system will be changed in the presence of light scattering matter over the sensor. The presence of light scattering matter over the sensor is expected to affect the intensity of both wavelengths used in sensing oxygen. Hence, as will come to be understood in the description herein, the extra intensity of detected light due to the presence of light scattering matter proximate the sensor can be determined based on the intensity of the wavelength that is not affected by changes in blood oxygen saturation.

Figure 1:
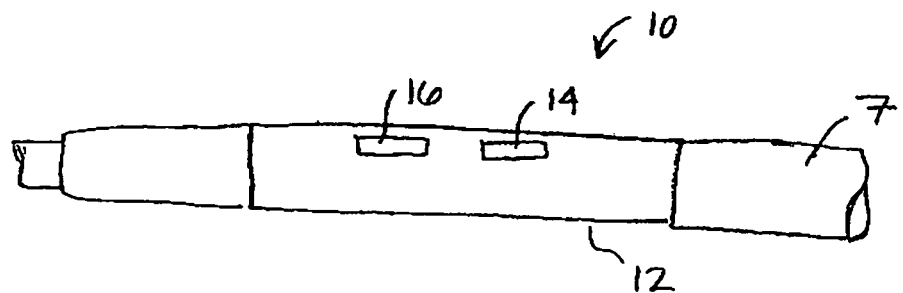
FIG. 1 is an enlarged view of an exemplary oxygen sensor assembly that may be included in an implantable medical lead and with which the present invention may be usefully practiced.

FIG. 1 is an enlarged view of an exemplary oxygen sensor assembly 10 that may be included in a medical lead and with which the present invention may be usefully practiced. An elongated sensor housing 12 is provided for housing oxygen sensor components. Lenses 14 and 16 are provided for passing emitted and reflected light from a light emitter and to a light detector, respectively, both of which reside within housing 12. Although a single lens may be used in lieu of two lenses. Lead body 7 is provided for carrying insulated conductors from the circuitry included in sensor assembly 10 to a connector assembly (not shown) located at a proximal end of the medical lead used for mechanically and electrically connecting the lead to an implantable medical device. A lead carrying oxygen sensor assembly 10 may additionally include other types of sensors and/or electrodes according to the intended use of the lead.

Figure 2:
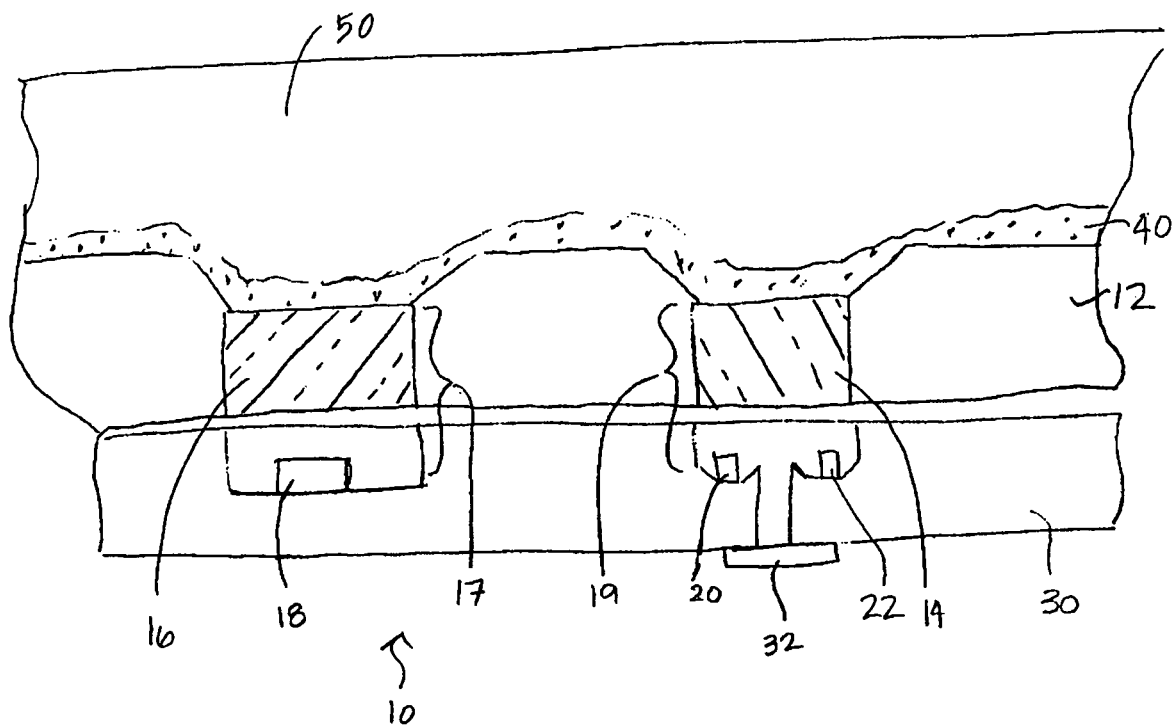
FIG. 2 is a sectional view of the oxygen sensor assembly of FIG. 1.

FIG. 2 is a sectional view of oxygen sensor assembly 10 of FIG. 1. Light emitters 20 and 22 are mounted on an oxygen sensor hybrid 30 in a light emitting portion 19 of oxygen sensor 10. Each light emitter 20 and 22 emits a different wavelength. Typically one of emitters 20 and 22 emits red light and the other of emitters 20 and 22 emits infrared light. Emitted light passes through lens 14 and must also pass through any tissue overgrowth 40 that is present on all or a portion of lens 14 before it enters blood volume 50. An optional self-test light detector 32 is shown in the light emitter portion 19 of oxygen sensor assembly 10. In one embodiment of the present invention, self-test light detector 32 is included for detecting the presence of tissue overgrowth as disclosed in the above-cited '290 patent issued to Miesel.

Light that is reflected from the blood volume 50 must pass through any tissue overgrowth 40 present over all or a portion of lens 16 before it reaches light detector 18. Light detector 18 is mounted on oxygen sensor hybrid 30 in a light detector portion 17 of oxygen sensor 10. Time intervals that are inversely proportional to the intensity of the received light signals associated with each of the two measured wavelengths, red and infrared, are measured as an electrical current induced in light detector 18 (which is preferably integrated over a capacitor included in the light detector 18). The presence of tissue overgrowth 40 generally reduces the light signal to noise ratio, as described previously, by both attenuating the reflected light signal associated with blood oxygen saturation and increasing noise due to extraneous light scattered by tissue overgrowth 40 reaching detector 18. The methods of the present invention address the latter problem of increased extraneous light received by detector 18, resulting in shortened time intervals, by correcting the measured time intervals for the amount of light signal attributed to noise.

Figure 3:
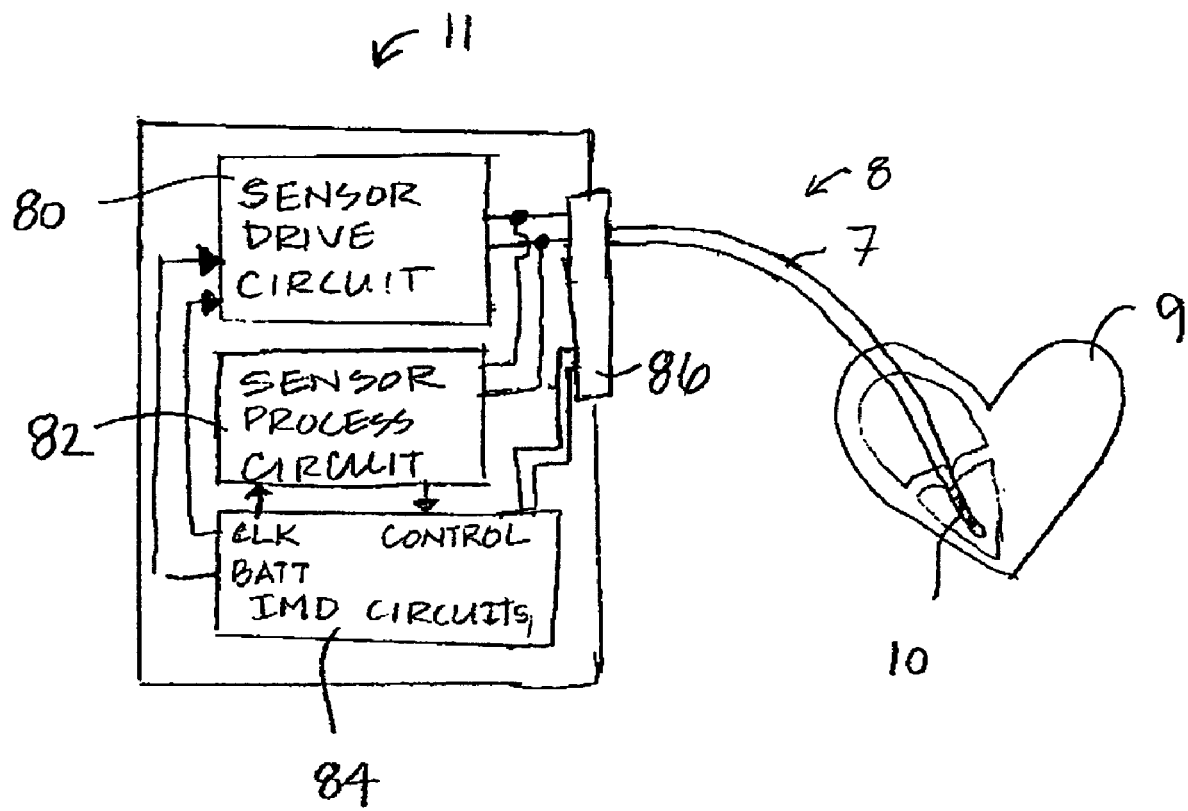
FIG. 3 shows a block diagram of an implantable medical device system including an implantable medical device (IMD) and medical electrical lead 8 having an optical sensor assembly for use in sensing blood oxygen saturation.

FIG. 3 shows a block diagram of an implantable medical device system including an implantable medical device (IMD) 11 and medical electrical lead 8 having an optical sensor assembly 10, for use in sensing blood oxygen saturation. Optical sensor 10 is typically mechanically and electrically coupled to the distal ends of lead conductors disposed within the body 7 of lead 8. Connector elements disposed at the proximal end of lead 8 are connected to the proximal ends of lead conductors and provide connection to sensor drive circuit 80 and sensor processor circuit 82 via a connector block 86. Sensor drive circuit 80 provides the operational power for optical sensor 10 and controls the timing of optical sensor operation. Sensor process circuit 82 receives optical sensor signal output and processes the signal output to estimate a measurement of blood oxygen saturation. In accordance with the present invention, the methods used by sensor process circuit 82 for estimating blood oxygen saturation includes calculations made to correct for the presence of tissue overgrowth covering a portion of or all of the lenses 14, 16 of optical sensor 10.

When IMD 11 includes cardiac pacing capabilities, lead 8 may additionally include pacing, sensing and/or defibrillation electrodes generally disposed at the distal end of lead 8 in operative relation to one or more heart chambers. Alternatively, additional pacing and sensing leads are included in the IMD system. Cardiac pacing and sensing control circuitry, a clock, and a battery for powering IMD operations are included in IMD circuits 84. Detailed descriptions of such circuitry included in an implantable medical device and its operation are provided in the above-incorporated '952 patent to Miesel.

Preferably, the reflection of red light (wavelength ~660 nm) and the reflection of infrared light (wavelength ~880 nm) are used for measuring blood oxygen saturation. The absorption of red light is a function of oxygen saturation and therefore the intensity of the reflected red light signal received by a light detector is inversely proportional to oxygen saturation. The absorption of infrared light is a function of non-oxygenated hemoglobin and hematocrit concentration. The ratio of the red light intensity to the infrared light intensity of the reflected light is used to normalize a measured light signal for changes in hematocrit and blood flow velocity. Prior art oxygen sensors therefore determine the blood oxygen saturation ($SAO_2$) according to the inverse relation to the reflected red light intensity normalized by the reflected infrared light intensity as shown by Equation (1):

(1) $SAO_2 = A + B(1/(R/IR))$ (2) wherein A and B are calibration constants defined by the intercept and slope of a calibration curve, respectively; IR is the intensity of reflected infrared light, and R is the intensity of reflected red light.

An alternative and commonly used form of Equation (1) takes the logarithm of the term including the ratio of the red to infrared light signal in order to linearize the function as shown in Equation (1'):

(1) $SAO_2 = A + B \log(1/(R/IR))$.     (1')

For the sake of simplicity, the methods described herein will be elaborated on with regard to Equation (1), but substitutions to be described in detail below to be made in Equation (1) for correcting for the presence of tissue overgrowth may be equivalently made in Equation (1').

(1) Equation (1) may be re-written as:

i. $SAO_2 = A + B(IR/R)$.

In accordance with the present invention, the terms R and IR in Equations (1) and (2) are corrected to account for increased light signal due to tissue overgrowth by subtracting the amount of red light and infrared light signal attributed to tissue overgrowth.

In correcting for the presence of tissue overgrowth, an assumption is made that the optical properties of the tissue overgrowth will affect both red and infrared light wavelengths and that the amount of red light reflected by tissue overgrowth will be proportional to the amount of infrared light reflected by tissue overgrowth. Another assumption made is that tissue overgrowth on the optical sensor has the same effect on sensor measurements as a shortened "dark interval." Herein, the term "dark interval" refers to the time interval measured from a photodetector in the absence of any true light signal reflected from the blood. The dark interval therefore is the time interval measured due to stray current or extraneous light reaching the photodetector such as light leakage from the emitter to the detector portion of the oxygen sensor. Hence, the presence of tissue overgrowth will increase extraneous light reaching the photodetector, causing a shortened dark interval. Another underlying assumption is that enough light is passed through the tissue to be reflected by the passing blood volume.

Based on the above assumptions, the "dark interval" measured in the presence of tissue overgrowth will include an infrared signal component and a red signal component. The infrared time interval contributing to the dark interval, $T_{IRdark}$, is given by Equation (3):

(1) $T_{IRdark} = 1/(IR - IR_{nominal})$     (3)

(2) wherein IR is the total infrared light signal received from all sources and $IR_{nominal}$ is the expected infrared light signal to be reflected from a blood pool when no tissue overgrowth is present.

The terms representing the IR and $IR_{nominal}$ light signals in Equation 3 can be replaced by the inverse of the time interval measured for each light signal. Hence, Equation (3) can be rewritten as:

(1) $T_{IRdark} = 1/((1/T_{IR}) - (1/T_{IRnom}))$     (4)

(2) wherein $T_{IR}$ is the time interval measured from the photodetector due to the total infrared light signal and $T_{IRnom}$ is the time interval measured from the photodetector due to the expected infrared light signal reflected from a blood pool in the absence of any tissue overgrowth.

As stated above, an assumption is made that the optical properties of the tissue cause red light to be reflected proportionally to infrared light. The time interval contribution to the dark interval from red light reflected from the tissue overgrowth, $T_{Rdark}$, can therefore be expressed as:

(1) $T_{Rdark} = K(T_{IRdark})$,     (5)

(2) wherein K is a correction factor that takes into account: 1) the ratio of red to infrared light intensities reflected from tissue overgrowth when red and infrared light sources emit equal intensities of red and infrared light, and 2) a scaling factor that represents the relative amplitudes of red and infrared light output power from the light emitters of the oxygen sensor. $T_{IRdark}$ is given by Equation (4) above.

A corrected red time interval, $T_{Rcorrected}$, for estimating oxygen saturation can be obtained from the inverse of the total red light signal received, R, less the red light signal attributed to the tissue overgrowth, $R_{dark}$:

(1) $T_{Rcorrected} = 1/(R - R_{dark})$.     (6)

(2) The terms R and $R_{dark}$ in Equation 6 may be substituted for by the inverse of the corresponding time intervals measured by the photodetector:

(3) $T_{Rcorrected} = 1/((1/T_R) - (1/T_{Rdark}))$,     (7)

(4) wherein $T_R$ is the time interval measured due to the total amount of reflected red light at the photodetector and $T_{Rdark}$ is given by Equation (5) above.

The corrected infrared time interval, $T_{IRcorrected}$, is simply equal to the time interval measured for infrared light reflected from a volume of blood in the absence of any tissue overgrowth:

(1) $T_{IRcorrected} = T_{IRnom}$ (8)

(2) Thus, in accordance with the present invention, Equation (2) above can be rewritten as:

(3) $SAO_2 = A + B(IR_{corrected}/R_{corrected})$, (9)

(4) which can be rewritten in terms of measured time intervals as:

(5) $SAO_2 = A + B(T_{Rcorrected}/T_{IRcorrected})$ (10)

By using Equations 4, 5, 7, and 8, to substitute for $T_{Rcorrected}$ and $T_{Ircorrected}$, and after mathematical simplification and reduction, Equation 10 can be equivalently rewritten as Equation 11 below in terms that are either measured or known quantities:

(1) $SAO_2 = A + B\{(K*T_R*T_{IRnom})/((K*T_{IR}*T_{IRnom}) - (T_R (T_{IRnom} - T_{IR})))\}$. (11)

As indicated previously, constants A and B are standard calibration constants; K is determined by experimentally measuring the ratio of red to infrared light reflected by tissue overgrowth upon exposure to equal intensities of emitted red and infrared light for a given sensor geometry and by knowing the relative output of the red and infrared light emitters of the oxygen sensor at the time of manufacture; $T_{IRnominal}$ is determined experimentally by measuring the infrared time interval due to infrared light reflected from a volume of blood in the absence of any tissue overgrowth; and $T_R$ and $T_{IR}$ are the time intervals measured from the photodetector associated with the intensity of red and infrared light reflected into the detector portion of the oxygen sensor during oxygen sensing operations.

Figure 4A:
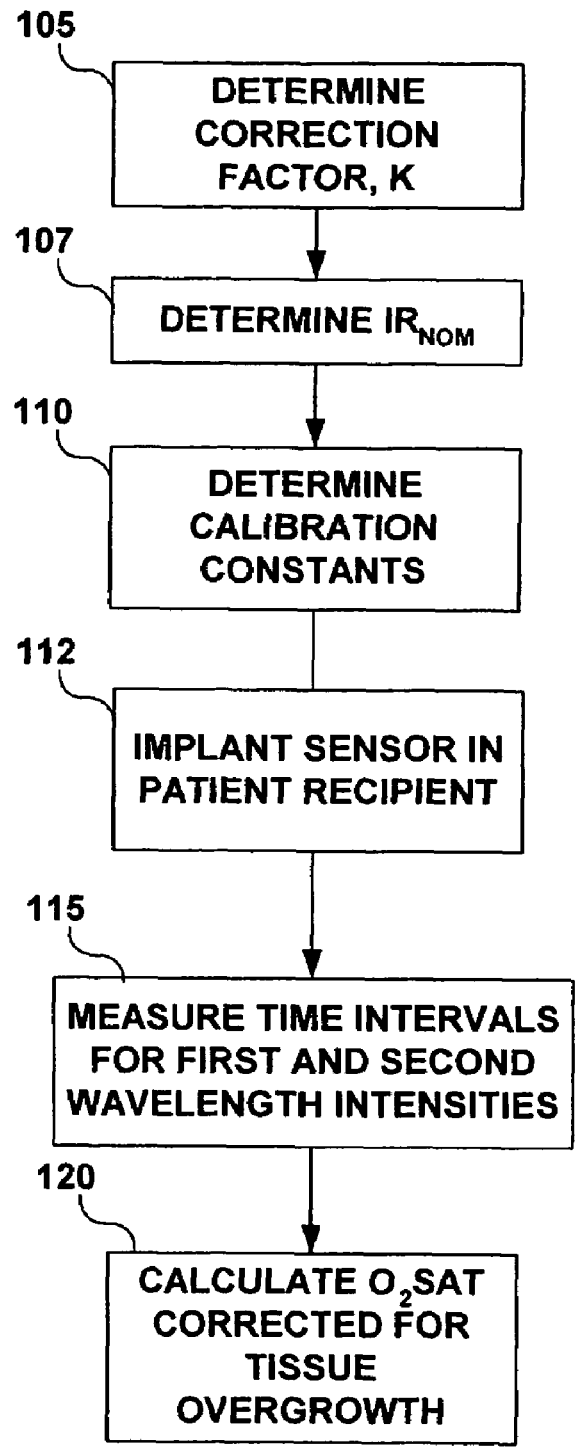
FIG. 4A is a flow chart summarizing steps included in a method for accurately estimating blood oxygen saturation using an implantable optical sensor independent of tissue overgrowth on the sensor.

FIG. 4A is a flow chart summarizing steps included in a method for accurately estimating blood oxygen saturation using an implantable optical sensor independent of tissue overgrowth on the sensor. Method 100 introduces the use of two new constants, K and $T_{IRnom}$, as defined above, in an equation for calculating oxygen saturation from optical sensor measurements. At step 105, the value for the tissue overgrowth correction factor, K, is obtained by experimentally quantifying the ratio of equally applied intensities of red light to infrared light reflected from tissue overgrowth for a given sensor geometry and multiplying this ratio by a scaling factor that represents the relative amplitudes of red and infrared light output power from the light emitters of the oxygen sensor as determined at the time of manufacture of the sensor. The ratio of reflected red to infrared light represents the light scattering and reflecting properties of tissue encapsulating a chronically implanted oxygen sensor. The scaling factor is known at the time of sensor manufacture.

At step 107, $T_{IRnom}$ is determined. $T_{IRnom}$ is also determined at the time of sensor manufacture and can be determined by measuring the reflected infrared light from a sample of material with known scattering and reflecting properties of IR light. $T_{IRnom}$ represents the return infrared light from a volume of blood at any known level of oxygen saturation.

At step 110 the calibration constants A and B are determined as the slope and offset of an oxygen saturation curve. These constants are also determined at the time of device manufacture, based upon experimental data to determine the response of a given sensor geometry, and the red and infrared output power of the emitters for an individual sensor. The determination and use of these calibration constants is known in the prior art.

Steps 105 through 110 are performed experimentally or at the time of sensor manufacture such that the constants, K, $T_{IRnom}$, A and B, may be programmed into firmware or software used by an implanted medical device in calculating oxygen saturation using signals received from the optical sensor. At step 112, the optical sensor is deployed with an associated IMD system by implanting the sensor at a desired location in the blood volume of a patient. Step 115 represents the normal operation of the optical sensor in which the intensities of red and infrared reflected light received at the light detector portion of the oxygen sensor are measured. At step 120, oxygen saturation is calculated according to Equation 11 above, based on the tissue overgrowth correction methodology provided by the present invention.

Figure 4B:
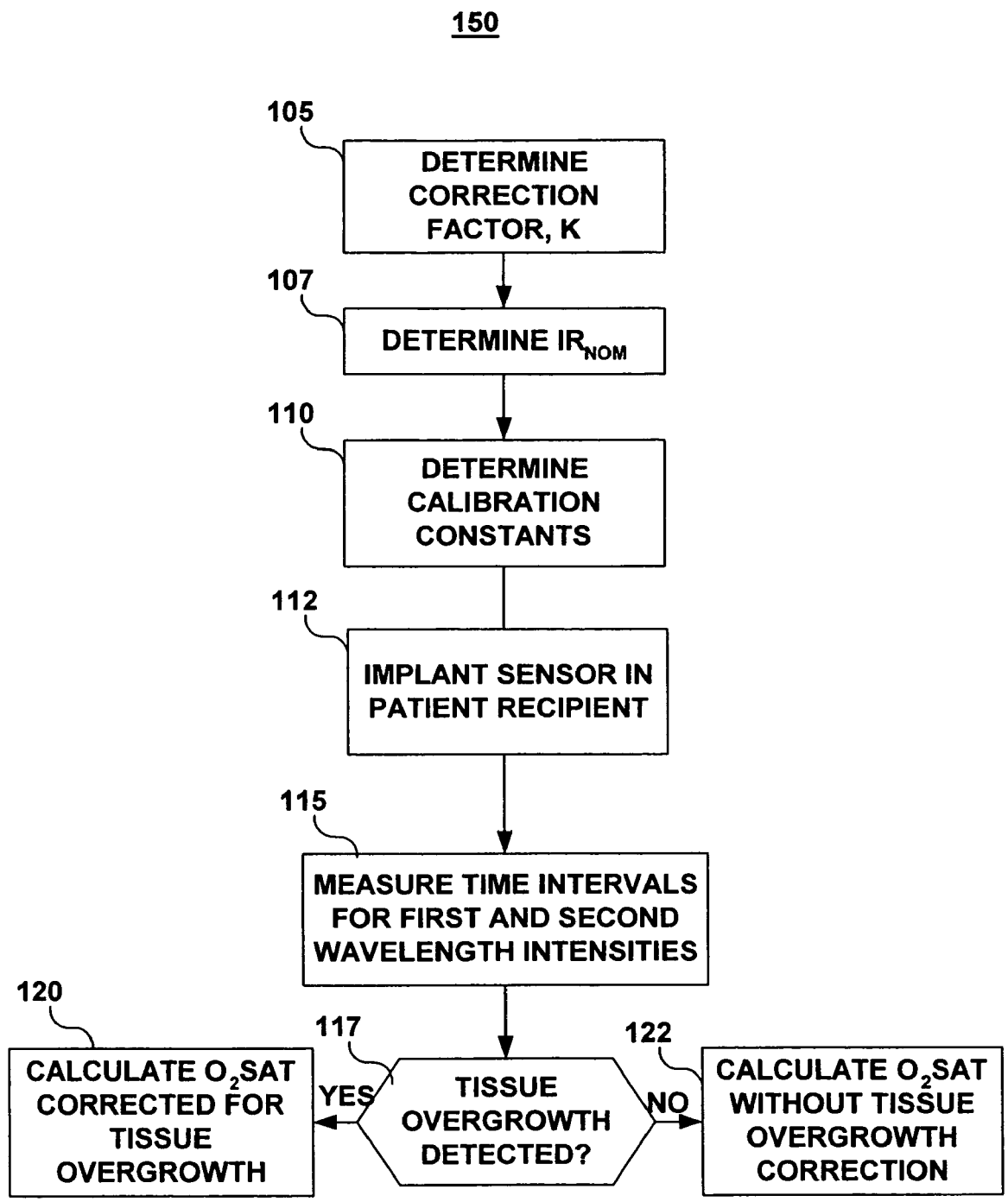
FIG. 4B is a flow chart summarizing steps included in an alternative method for accurately estimating blood oxygen saturation using an implantable optical sensor independent of tissue overgrowth on the sensor.

FIG. 4B is a flow chart summarizing steps included in an alternative method for accurately estimating blood oxygen saturation using an implantable optical sensor independent of tissue overgrowth on the sensor. Identically labeled steps included in method 150 correspond to the same steps included in method 100, described above. However, method 150 includes a decision step 117 for determining if tissue overgrowth is present. Tissue overgrowth may be detected by the use of a self-test light detector in the emitter portion of the oxygen sensor, as generally disclosed in the above-cited '290 patent to Miesel. When tissue overgrowth is detected, Equation 11 is used by sensor processing circuitry of the implantable medical device for calculating oxygen saturation corrected for the presence of tissue overgrowth at step 120. If tissue overgrowth is not detected at decision step 117, Equation 2 may be used by sensor processing circuitry for calculating oxygen saturation without correcting for the presence of tissue overgrowth at step 122.

Figure 5:
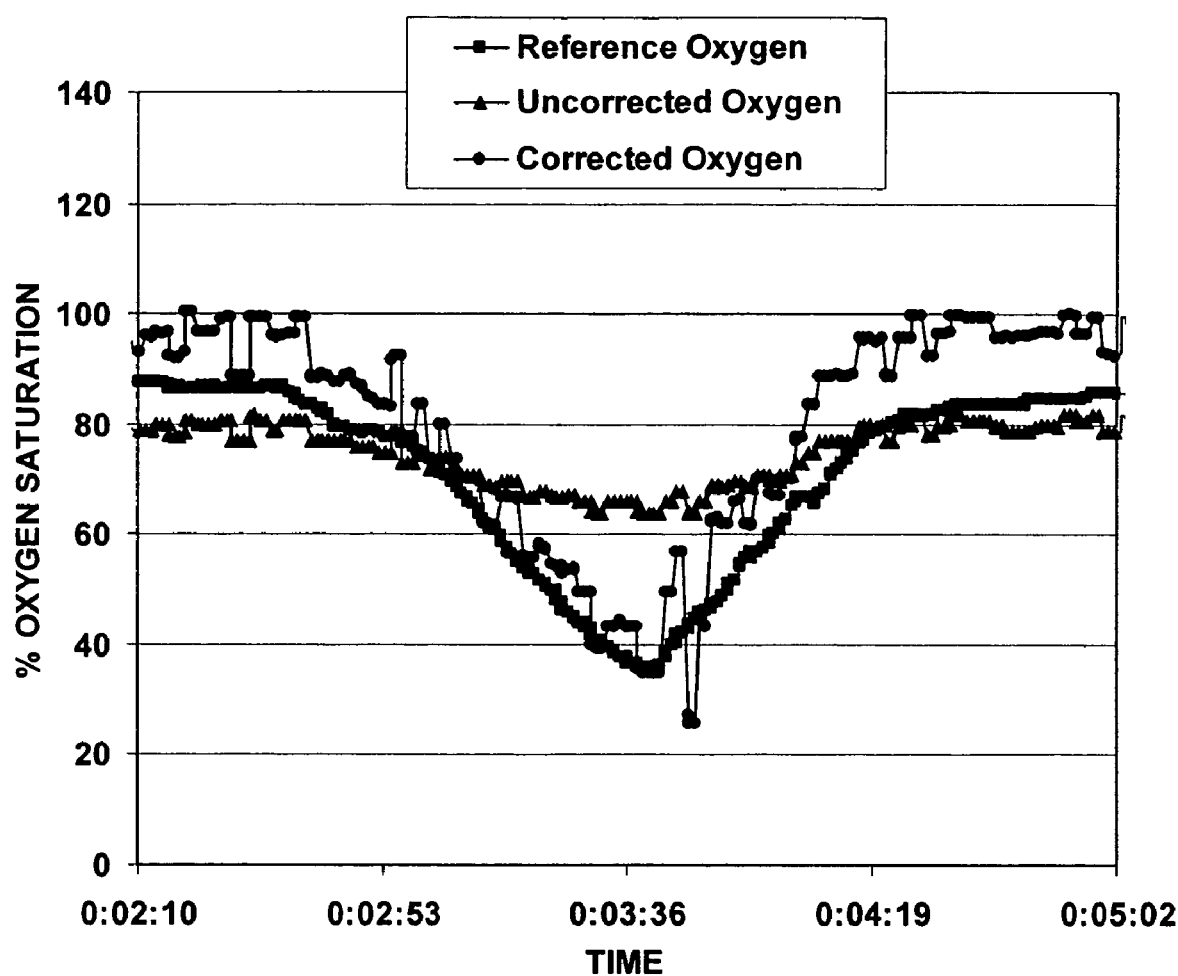
FIG. 5 is a graph of oxygen saturation measurements made from a chronically implanted oxygen sensor having tissue overgrowth based on prior art methods and based on the tissue overgrowth correction method provided by the present invention plotted in comparison to a reference oxygen saturation measurement.

FIG. 5 is a graph of experimental oxygen saturation measurements made from a chronically implanted oxygen sensor having tissue overgrowth based on prior art methods and based on the tissue overgrowth correction method provided by the present invention plotted compared to a reference oxygen saturation measurement. The graph is exemplary of the operation of an oxygen sensor with and without the tissue overgrowth correction method. The graph shows the results of oxygen saturation measurements obtained from a chronically implanted oxygen sensor and an acutely implanted reference oxygen saturation sensor during an oxygen desaturation experiment. Oxygen desaturation was accomplished in a sedated canine by temporarily introducing helium into the respirator, causing reduction in the uptake of oxygen.

Reference oxygen sensor measurements (square symbols) show a decrease in oxygen saturation followed by a return to normal oxygen saturation levels after respirator oxygen levels had been restored. The chronically implanted oxygen sensor in this canine has been overgrown with fibrin, causing a lack of response in the oxygen values determined without correcting for tissue overgrowth (triangle symbol) compared to the reference oxygen sensor measurements.

The tissue overgrowth correction in this example was determined using red and infrared time intervals recorded at the time of implant, rather than at the time of manufacture, since tissue response had not been determined for the sensor before manufacture. The correction was performed using time intervals extracted from the oxygen saturation and the measured infrared time intervals, since the red time intervals were not recorded as part of the original study. This causes a decrease in resolution in the corrected oxygen saturation measurement that would not be present in a system that either compensates the signals before recording, or with a system that records the red time interval along with the IR time interval as described above.

However, it can be seen from the graph of FIG. 5 that the response of the corrected oxygen saturation measurements made from the chronically implanted, tissue overgrown sensor (circle symbols), responds to the desaturation event similarly to the reference oxygen sensor measurements, while the uncorrected oxygen saturation measurements show an attenuated response to the desaturation event.

Thus, a system and method are provided for accurately estimating blood oxygen saturation from optical sensor measurements independent of the presence of encapsulating tissue over all or a portion of the optical sensor. Methods included in the present invention have been described with regard to an optical oxygen sensor application. However, it is contemplated that tissue overgrowth correction methodologies provided by the present invention may be applied in the use of other types of implantable optical sensors employing a two-wavelength system, such as glucose sensors. Depending on the wavelengths employed, the tissue overgrowth correction factor, K, may not be a constant if the optical properties of the tissue overgrowth affect the normalizing wavelength differently than the targeted measurement wavelength. Therefore, while the present invention has been described according to specific embodiments presented herein, aspects of the present invention may be applied in alternative embodiments including implantable, two-wavelength optical sensor systems. As such the disclosed embodiments are intended to be exemplary, not limiting, with regard to the following claims.

The invention claimed is:

1. A method for accurately estimating an oxygen saturation metric for a volume of blood by an optical sensor measurement, comprising:
   deploying a dual wavelength optical sensor into fluid communication with a volume of blood, wherein said volume of blood is characterized by a blood flow rate condition, said flow rate condition comprising one of: relatively low, stasis, substantially stagnant;
   determining a tissue overgrowth correction factor (K) for a first and a second wavelength of optical radiation in the dual wavelength optical sensor, wherein said first wavelength of optical radiation is substantially proportional to an amount of saturated oxygen present in said volume of blood and said second wavelength of radiation is substantially independent of the amount of saturated oxygen present in the volume of blood;
   determining a nominal time interval for detecting the second wavelength of optical radiation (T2) after it is directed to a volume of blood having known optical properties;
   determining a pair of calibration constants (A,B) for said first and said second wavelength of optical radiation;
   measuring a first time interval for the first wavelength of radiation and a second time interval for the second wavelength of radiation when said first and second wavelengths of radiation are directed to the volume of blood; and
   calculating a saturation metric for the saturated oxygen based upon the tissue overgrowth correction factor (K), the pair of calibration constants (A,B), the nominal time interval, the first time interval and the second time interval.

2. A method according to claim 1, wherein the calculating step further comprises: calculating oxygen saturation ($SAO_2$) according to the following mathematical expression:

$$SAO_2 = A + B\{(K^* T_R^* T_{IRnom})/((K^* T_{IR}^* T_{IRnom}) - (T_R (T_{IRnom} T_{IR})))\}$$, wherein $T_R$ is the first time interval, $T_{IR}$ is the second time interval and $T_{IRnom}$ is the nominal time interval.

3. A method according to claim 1, further comprising providing an oxygen saturation metric output signal.

4. A method according to claim 1, wherein after measuring the first time interval and the second time interval, performing the step of:
   detecting a tissue overgrowth condition, and if the tissue overgrowth condition is positive then: calculating a corrected oxygen saturation metric; and
   if the tissue overgrowth condition is negative then: calculating an uncorrected oxygen saturation metric.

5. A method according to claim 1, wherein the first wavelength of optical radiation is approximately 660 nm and the second wavelength of radiation is approximately 880 nm.

6. A method according to claim 1, wherein the dual wavelength optical sensor is disposed in a volume of blood proximate an implantable medical device.

7. A method according to claim 6, wherein the implantable medical device comprises: an implantable heart monitor, a pacemaker, a cardioverter-defibrillator, a myostimulation device, a nerve stimulation device, a drug delivery device.

8. A method according to claim 1, wherein said dual wavelength optical sensor mechanically couples to an implantable medical device.

9. A method according to claim 1, wherein the oxygen saturation metric comprises a saturated arterial oxygen metric.

10. A system for accurately estimating an oxygen saturation metric for a volume of blood, comprising:
    means for determining a tissue overgrowth correction factor (K) for a first and a second wavelength of optical radiation in a dual wavelength optical sensor, wherein said first wavelength of optical radiation is substantially proportional to saturated oxygen present in a volume of blood and said second wavelength of radiation is substantially independent of saturated oxygen;
    means for determining a nominal time interval for detecting the second wavelength of optical radiation (T2) after it is directed to the volume of blood having known optical properties;
    means for determining a pair of calibration constants (A,B) for said first and said second wavelength of optical radiation;
    means for placing the dual wavelength optical sensor in the volume of blood, wherein said volume of blood is characterized by a blood flow-rate condition, said flow-rate condition comprising one of: relatively low, stasis, substantially stagnant;
    means for measuring a first time interval for the first wavelength of radiation and a second time interval for the second wavelength of radiation when said first and second wavelengths of radiation are directed to the volume of blood; and
    means for calculating a saturation metric for a metabolite of interest based upon the tissue overgrowth correction factor (K), the pair of calibration constants (A,B), the nominal time interval, the first time interval and the second time interval.

11. A system according to claim 10, further comprising means for calculating oxygen saturation $SAO_2$ for the volume of blood according to the following mathematical expression:

$SAO_2 = A + B\{(K*T_R*T_{IRnom})/((K*T_{IR}*T_{IRnom}) - (T_R(T_{IRnom} - T_{IR})))\}$, wherein $T_R$ is the first time interval, $T_{IR}$ is the second time interval and $T_{IRnom}$ is the nominal time interval.

12. A system according to claim 10, further comprising providing an oxygen saturation-metric output signal.

13. A system according to claim 10, further comprising:
means for detecting a tissue overgrowth condition, and
wherein if the tissue overgrowth condition is positive then calculating a corrected oxygen saturation metric; and
wherein if the tissue overgrowth condition is negative then calculating an uncorrected oxygen saturation metric.

14. A system according to claim 10, wherein the first wavelength of optical radiation is approximately 660 nm and the second wavelength of radiation is approximately 880 nm.

15. A system according to claim 10, wherein the dual wavelength optical sensor is configured to be disposed in the volume of blood proximate an implantable medical device.

16. A system according to claim 15, wherein the implantable medical device comprises one of: an implantable heart monitor, a pacemaker, a cardioverter-defibrillator, a myo-stimulation device, a nerve stimulation device, a drug delivery device.

17. A system according to claim 10, wherein said dual wavelength optical sensor mechanically couples to an implantable medical device.

18. A system according to claim 10, wherein the oxygen saturation comprises an arterial oxygen saturation metric.

* * * * *